(12) United States Patent
Kostrzewski

(10) Patent No.: US 8,931,681 B2
(45) Date of Patent: Jan. 13, 2015

(54) SURGICAL INSTRUMENT AND CARTRIDGE FOR USE THEREWITH

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/275,929

(22) Filed: May 13, 2014

(65) Prior Publication Data

US 2014/0249549 A1    Sep. 4, 2014

Related U.S. Application Data

(63) Continuation of application No. 13/173,295, filed on Jun. 30, 2011, now Pat. No. 8,763,876.

(51) Int. Cl.
*A61B 17/068* (2006.01)
*A61B 17/10* (2006.01)
(Continued)

(52) U.S. Cl.
CPC .......... *A61B 17/105* (2013.01); *A61B 17/07207* (2013.01); *A61B 2017/00473* (2013.01); *A61B 2017/07228* (2013.01); *A61B 2017/07271* (2013.01); *A61B 2017/07278* (2013.01);
(Continued)

(58) Field of Classification Search
CPC ............. A61B 17/068; A61B 17/0686; A61B 17/072; A61B 17/07207; A61B 17/07292
USPC ............... 227/19, 175.1, 176.1, 175.2, 178.1, 227/180.1; 606/139, 153, 219
See application file for complete search history.

(56) References Cited

U.S. PATENT DOCUMENTS

| 3,079,606 | A | 3/1963 | Bobrov et al. |
| 3,490,675 | A | 1/1970 | Green et al. |

(Continued)

FOREIGN PATENT DOCUMENTS

| AU | 5476586 A | 9/1986 |
| CA | 2773414 A1 | 11/2012 |

(Continued)

OTHER PUBLICATIONS

European Search Report dated Mar. 6, 2013 from counterpart EP Application No. 12173998.1 (14 pgs.).

(Continued)

*Primary Examiner* — Scott A. Smith

(57) ABSTRACT

A cartridge assembly is disclosed. The cartridge assembly comprises a cartridge housing and a cartridge. The cartridge housing has a plurality of biasing members thereon. The cartridge is configured for reception at least partially within the cartridge housing. The cartridge includes a plurality of fasteners at least partially therein. The cartridge has a plurality of pockets. Each fastener is ejectable from a corresponding pocket. The cartridge has a plurality of chambers, and each chamber is adjacent a pocket and configured to store at least one fastener at least partially therein. At least one fastener is movable from the chamber to the pocket. The cartridge includes a plurality of pushers, where each pusher is configured to engage at least one corresponding fastener. At least one pusher includes at least one cam surface thereon. Each biasing member urges at least one corresponding fastener toward the corresponding pocket.

17 Claims, 14 Drawing Sheets

(51) Int. Cl.
*A61B 17/072* (2006.01)
*A61B 17/00* (2006.01)
*A61B 17/29* (2006.01)

(52) U.S. Cl.
CPC ................ *A61B2017/07221* (2013.01); *A61B 2017/07285* (2013.01); *A61B 2017/2933* (2013.01); *A61B 17/068* (2013.01)
USPC ....... 227/176.1; 227/19; 227/180.1; 606/139; 606/219

(56) References Cited

U.S. PATENT DOCUMENTS

| | | |
|---|---|---|
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,821,721 A | 4/1989 | Chin et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,190,560 A | 3/1993 | Woods et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |

(56) References Cited

U.S. PATENT DOCUMENTS

| | | |
|---|---|---|
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,738,474 A | 4/1998 | Blewett |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |

(56) References Cited

U.S. PATENT DOCUMENTS

| | | |
|---|---|---|
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielsen et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,556,185 B2 | 7/2009 | Viola |
| 7,556,186 B2 | 7/2009 | Milliman |

(56) References Cited

U.S. PATENT DOCUMENTS

| | | |
|---|---|---|
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,594,920 B2 | 9/2009 | Kayan et al. |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,666,194 B2 | 2/2010 | Field et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,721,933 B2 | 5/2010 | Ehrenfels et al. |
| 7,726,538 B2 | 6/2010 | Holsten et al. |
| 7,726,539 B2 | 6/2010 | Holsten et al. |
| 7,740,160 B2 | 6/2010 | Viola |
| 7,744,628 B2 | 6/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,760 B2 | 11/2010 | Zemlok et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,918,866 B2 | 4/2011 | Geitz |
| 7,922,061 B2 | 4/2011 | Shelton, IV et al. |
| 7,922,063 B2 | 4/2011 | Zemlok et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |

(56) References Cited

U.S. PATENT DOCUMENTS

| | | |
|---|---|---|
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,020,742 B2 | 9/2011 | Marczyk |
| 8,028,882 B2 | 10/2011 | Viola |
| 8,028,883 B2 | 10/2011 | Stopek |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,763,876 B2 | 7/2014 | Kostrzewski |
| 2004/0007608 A1 | 1/2004 | Ehrenfels et al. |
| 2004/0050902 A1 | 3/2004 | Green et al. |
| 2004/0093029 A1 | 5/2004 | Zubik et al. |
| 2004/0094597 A1 | 5/2004 | Whitman et al. |
| 2004/0108357 A1 | 6/2004 | Milliman et al. |
| 2004/0149802 A1 | 8/2004 | Whitman |
| 2004/0173659 A1 | 9/2004 | Green et al. |
| 2004/0199180 A1 | 10/2004 | Knodel et al. |
| 2004/0199181 A1 | 10/2004 | Knodel et al. |
| 2004/0232199 A1 | 11/2004 | Shelton et al. |
| 2004/0232200 A1 | 11/2004 | Shelton et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2004/0267311 A1 | 12/2004 | Viola et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006432 A1 | 1/2005 | Racenet et al. |
| 2005/0006433 A1 | 1/2005 | Milliman et al. |
| 2005/0006434 A1 | 1/2005 | Wales et al. |
| 2005/0023324 A1 | 2/2005 | Doll et al. |
| 2005/0023325 A1 | 2/2005 | Gresham et al. |
| 2005/0067457 A1 | 3/2005 | Shelton et al. |
| 2005/0067458 A1 | 3/2005 | Swayze et al. |
| 2005/0067459 A1 | 3/2005 | Swayze et al. |
| 2005/0067460 A1 | 3/2005 | Milliman et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet et al. |
| 2005/0119669 A1 | 6/2005 | Demmy |
| 2005/0127131 A1 | 6/2005 | Mastri et al. |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton |
| 2005/0178813 A1 | 8/2005 | Swayze et al. |
| 2005/0184121 A1 | 8/2005 | Heinrich |
| 2005/0184123 A1 | 8/2005 | Scirica |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0263562 A1 | 12/2005 | Shelton et al. |
| 2005/0279804 A1 | 12/2005 | Scirica et al. |
| 2006/0000867 A1 | 1/2006 | Shelton et al. |
| 2006/0000868 A1 | 1/2006 | Shelton et al. |
| 2006/0011699 A1 | 1/2006 | Olson et al. |
| 2006/0016853 A1 | 1/2006 | Racenet |
| 2006/0022014 A1 | 2/2006 | Shelton et al. |
| 2006/0022015 A1 | 2/2006 | Shelton et al. |
| 2006/0025809 A1 | 2/2006 | Shelton |
| 2006/0043147 A1 | 3/2006 | Mastri et al. |
| 2006/0049229 A1 | 3/2006 | Milliman et al. |
| 2006/0049230 A1 | 3/2006 | Shelton et al. |
| 2006/0060630 A1 | 3/2006 | Shelton et al. |
| 2006/0081678 A1 | 4/2006 | Ehrenfels et al. |
| 2006/0097026 A1 | 5/2006 | Shelton |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0175375 A1 | 8/2006 | Shelton et al. |
| 2006/0180634 A1 | 8/2006 | Shelton et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton |
| 2007/0045380 A1 | 3/2007 | Mastri et al. |
| 2007/0068989 A1 | 3/2007 | Shelton |
| 2007/0068990 A1 | 3/2007 | Shelton et al. |
| 2007/0073340 A1 | 3/2007 | Shelton et al. |
| 2007/0073341 A1 | 3/2007 | Smith et al. |
| 2007/0075114 A1 | 4/2007 | Shelton et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton et al. |
| 2007/0084896 A1 | 4/2007 | Doll et al. |
| 2007/0084897 A1 | 4/2007 | Shelton et al. |
| 2007/0084898 A1 | 4/2007 | Scirica |
| 2007/0084899 A1 | 4/2007 | Taylor |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0102476 A1 | 5/2007 | Shelton et al. |
| 2007/0106317 A1 | 5/2007 | Shelton et al. |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |

(56) References Cited

U.S. PATENT DOCUMENTS

| | | |
|---|---|---|
| 2007/0170225 A1 | 7/2007 | Shelton et al. |
| 2007/0175947 A1 | 8/2007 | Ortiz et al. |
| 2007/0175948 A1 | 8/2007 | Scirica et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175954 A1 | 8/2007 | Viola |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |
| 2007/0175964 A1 | 8/2007 | Shelton et al. |
| 2007/0179528 A1 | 8/2007 | Soltz et al. |
| 2007/0187453 A1 | 8/2007 | Smith et al. |
| 2007/0187454 A1 | 8/2007 | Scirica |
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0050671 A1 | 2/2009 | Racenet et al. |
| 2009/0057370 A1 | 3/2009 | Marczyk et al. |
| 2009/0065549 A1 | 3/2009 | Viola |
| 2009/0065550 A1 | 3/2009 | Green et al. |
| 2009/0065551 A1 | 3/2009 | Green et al. |
| 2009/0065552 A1 | 3/2009 | Knodel et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok et al. |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green et al. |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffin et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1 | 11/2009 | Viola et al. |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0314820 A1 | 12/2009 | Green et al. |
| 2009/0314821 A1 | 12/2009 | Racenet |
| 2010/0001036 A1 | 1/2010 | Marczyk et al. |
| 2010/0006620 A1 | 1/2010 | Sorrentino et al. |
| 2010/0012702 A1 | 1/2010 | Marczyk |
| 2010/0012703 A1 | 1/2010 | Calabrese et al. |
| 2010/0012704 A1 | 1/2010 | Tarinelli Racenet et al. |
| 2010/0025452 A1 | 2/2010 | Whitman |

(56) References Cited

U.S. PATENT DOCUMENTS

| | | |
|---|---|---|
| 2010/0032470 A1 | 2/2010 | Hess et al. |
| 2010/0044411 A1 | 2/2010 | Viola |
| 2010/0065605 A1 | 3/2010 | Shelton, VI et al. |
| 2010/0065606 A1 | 3/2010 | Stopek |
| 2010/0065608 A1 | 3/2010 | Olson et al. |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072255 A1 | 3/2010 | Olson et al. |
| 2010/0072256 A1 | 3/2010 | Baxter, III et al. |
| 2010/0072257 A1 | 3/2010 | Farascioni |
| 2010/0072258 A1 | 3/2010 | Farascioni et al. |
| 2010/0076429 A1 | 3/2010 | Heinrich |
| 2010/0076459 A1 | 3/2010 | Farascioni |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096432 A1 | 4/2010 | Scirica |
| 2010/0096433 A1 | 4/2010 | Mastri et al. |
| 2010/0096434 A1 | 4/2010 | Viola et al. |
| 2010/0108739 A1 | 5/2010 | Holsten et al. |
| 2010/0116867 A1 | 5/2010 | Balbierz et al. |
| 2010/0116868 A1 | 5/2010 | Prommersberger |
| 2010/0127040 A1 | 5/2010 | Smith et al. |
| 2010/0127041 A1 | 5/2010 | Morgan et al. |
| 2010/0127042 A1 | 5/2010 | Shelton, IV |
| 2010/0127043 A1 | 5/2010 | Olson et al. |
| 2010/0133317 A1 | 6/2010 | Shelton, IV et al. |
| 2010/0133318 A1 | 6/2010 | Boudreaux |
| 2010/0133319 A1 | 6/2010 | Milliman et al. |
| 2010/0133321 A1 | 6/2010 | Racenet et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0163596 A1 | 7/2010 | Marczyk |
| 2010/0163597 A1 | 7/2010 | Shah et al. |
| 2010/0170931 A1 | 7/2010 | Viola |
| 2010/0170933 A1 | 7/2010 | Ivanko |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0237131 A1 | 9/2010 | Milliman et al. |
| 2010/0237133 A1 | 9/2010 | Shah |
| 2010/0243706 A1 | 9/2010 | Cohen et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0243710 A1 | 9/2010 | Mastri et al. |
| 2010/0243711 A1 | 9/2010 | Olson et al. |
| 2010/0249802 A1 | 9/2010 | May et al. |
| 2010/0252610 A1 | 10/2010 | Viola |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0270356 A1 | 10/2010 | Holsten et al. |
| 2010/0282816 A1 | 11/2010 | Scirica et al. |
| 2010/0282817 A1 | 11/2010 | Ehrenfels et al. |
| 2010/0282819 A1 | 11/2010 | Racenet et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308099 A1 | 12/2010 | Marczyk et al. |
| 2010/0308100 A1 | 12/2010 | Boudreaux |
| 2010/0320252 A1 | 12/2010 | Viola et al. |
| 2010/0320253 A1 | 12/2010 | Marczyk |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0024480 A1 | 2/2011 | Marczyk |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036893 A1 | 2/2011 | Viola |
| 2011/0036895 A1 | 2/2011 | Marczyk et al. |
| 2011/0042439 A1 | 2/2011 | Johnson et al. |
| 2011/0042440 A1 | 2/2011 | Holsten et al. |
| 2011/0042441 A1 | 2/2011 | Shelton, IV et al. |
| 2011/0062212 A1 | 3/2011 | Shelton, IV et al. |
| 2011/0062213 A1 | 3/2011 | Scirica et al. |
| 2011/0068144 A1 | 3/2011 | Krehel |
| 2011/0068145 A1 | 3/2011 | Bedi et al. |
| 2011/0068146 A1 | 3/2011 | Viola et al. |
| 2011/0068148 A1 | 3/2011 | Hall et al. |
| 2011/0079626 A1 | 4/2011 | Viola et al. |
| 2011/0079628 A1 | 4/2011 | Racenet et al. |
| 2011/0084112 A1 | 4/2011 | Kostrzewski |
| 2011/0084113 A1 | 4/2011 | Bedi et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089220 A1 | 4/2011 | Ingmanson et al. |
| 2011/0089221 A1 | 4/2011 | Masiakos et al. |
| 2011/0095067 A1 | 4/2011 | Ohdaira |
| 2011/0101066 A1 | 5/2011 | Farascioni et al. |
| 2011/0101067 A1 | 5/2011 | Johnson et al. |
| 2011/0101069 A1 | 5/2011 | Bombard et al. |
| 2011/0101070 A1 | 5/2011 | Bettuchi et al. |
| 2011/0108603 A1 | 5/2011 | Racenet et al. |
| 2011/0108605 A1 | 5/2011 | Sapienza |
| 2011/0108606 A1 | 5/2011 | Whitman |
| 2011/0114702 A1 | 5/2011 | Farascioni |
| 2011/0121049 A1 | 5/2011 | Malinouskas et al. |
| 2011/0121050 A1 | 5/2011 | Nicholas et al. |
| 2011/0121051 A1 | 5/2011 | Shelton, IV et al. |
| 2011/0121052 A1 | 5/2011 | Shelton, IV et al. |
| 2011/0132960 A1 | 6/2011 | Whitman et al. |
| 2011/0132961 A1 | 6/2011 | Whitman et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155784 A1 | 6/2011 | Shelton, IV et al. |
| 2011/0155785 A1 | 6/2011 | Laurent et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163148 A1 | 7/2011 | Wenchell et al. |
| 2011/0163149 A1 | 7/2011 | Viola |
| 2011/0163150 A1 | 7/2011 | Farascioni |
| 2011/0168756 A1 | 7/2011 | Racenet et al. |
| 2011/0168757 A1 | 7/2011 | Viola et al. |
| 2011/0168758 A1 | 7/2011 | Mastri et al. |
| 2011/0168759 A1 | 7/2011 | Prommersberger |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0180586 A1 | 7/2011 | Shah |
| 2011/0184443 A1 | 7/2011 | Tzakis et al. |
| 2011/0186614 A1 | 8/2011 | Kasvikis |

(56) References Cited

U.S. PATENT DOCUMENTS

| | | |
|---|---|---|
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0192884 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0233260 A1 | 9/2011 | Milliman et al. |
| 2011/0240711 A1 | 10/2011 | Scirica |
| 2011/0240712 A1 | 10/2011 | Kostrzewski |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0253766 A1 | 10/2011 | Baxter, III et al. |
| 2011/0257679 A1 | 10/2011 | Ishitsuki et al. |
| 2012/0138660 A1 | 6/2012 | Shelton, IV |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399699 A1 | 11/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1785098 | 5/2007 |
| EP | 1785098 A2 | 5/2007 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| SU | 659146 A1 | 4/1979 |
| SU | 728848 A1 | 4/1980 |
| SU | 980703 A1 | 12/1982 |
| SU | 990220 A1 | 1/1983 |
| WO | 8302247 | 7/1983 |
| WO | 89/10094 A1 | 11/1989 |
| WO | 9210976 A1 | 7/1992 |
| WO | 9308754 A1 | 5/1993 |
| WO | 9314706 A1 | 8/1993 |
| WO | WO 2009/029065 A1 | 3/2009 |
| WO | 2010/054404 A1 | 5/2010 |
| WO | WO 2010/054404 A1 | 5/2010 |

OTHER PUBLICATIONS

European Search Report for EP 12196800.2-1654 date of completion is Feb. 28, 2013 (5 pages).

Partial European Search Report for EP 12173998.1-1654 date of completion is Feb. 27, 2013 (13 pages).

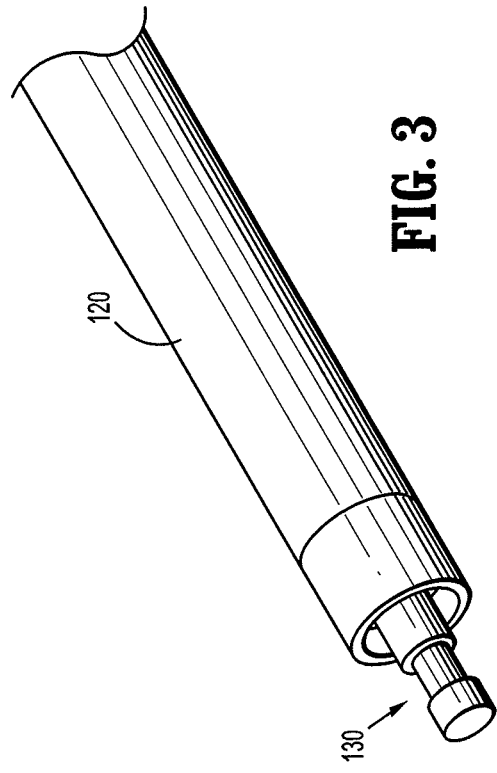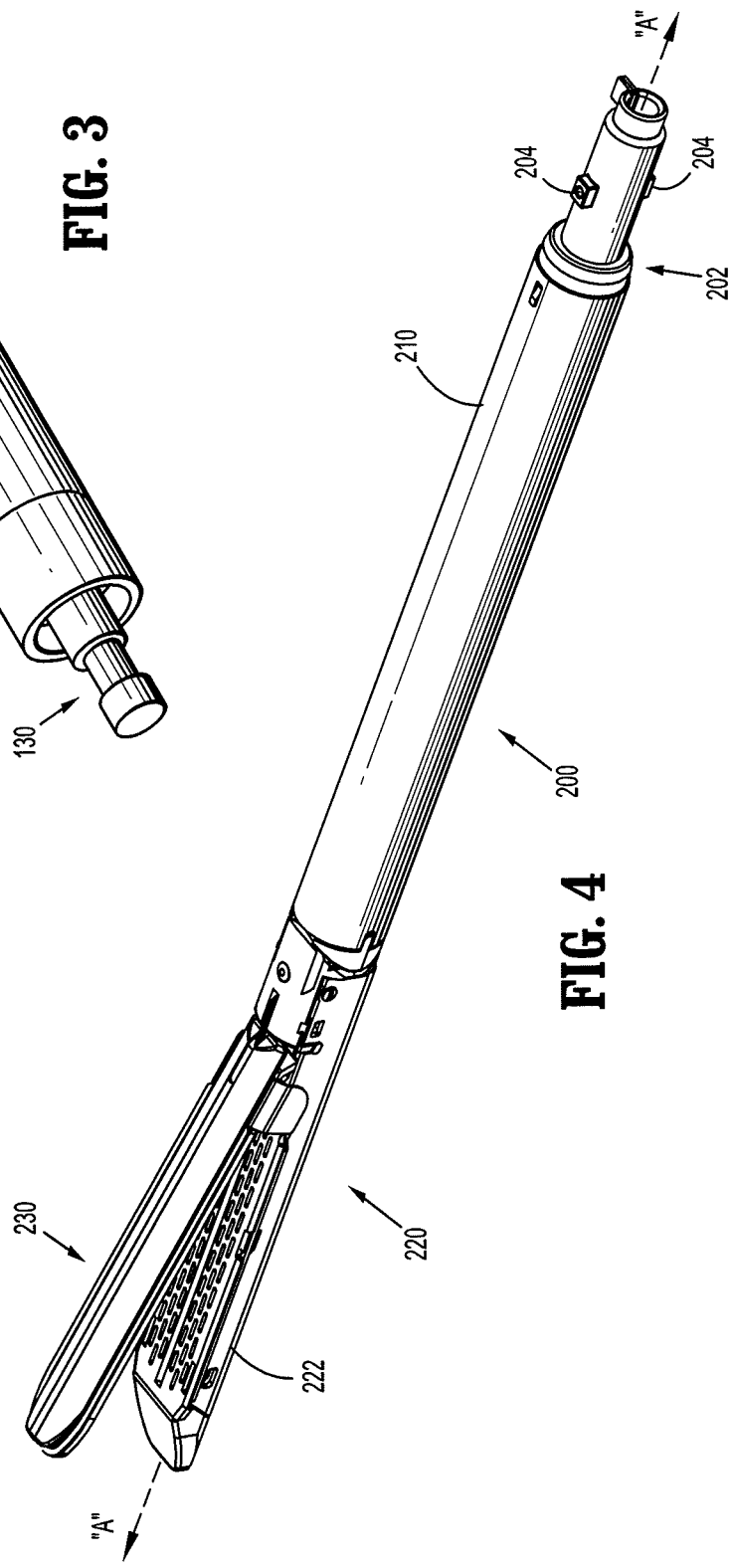

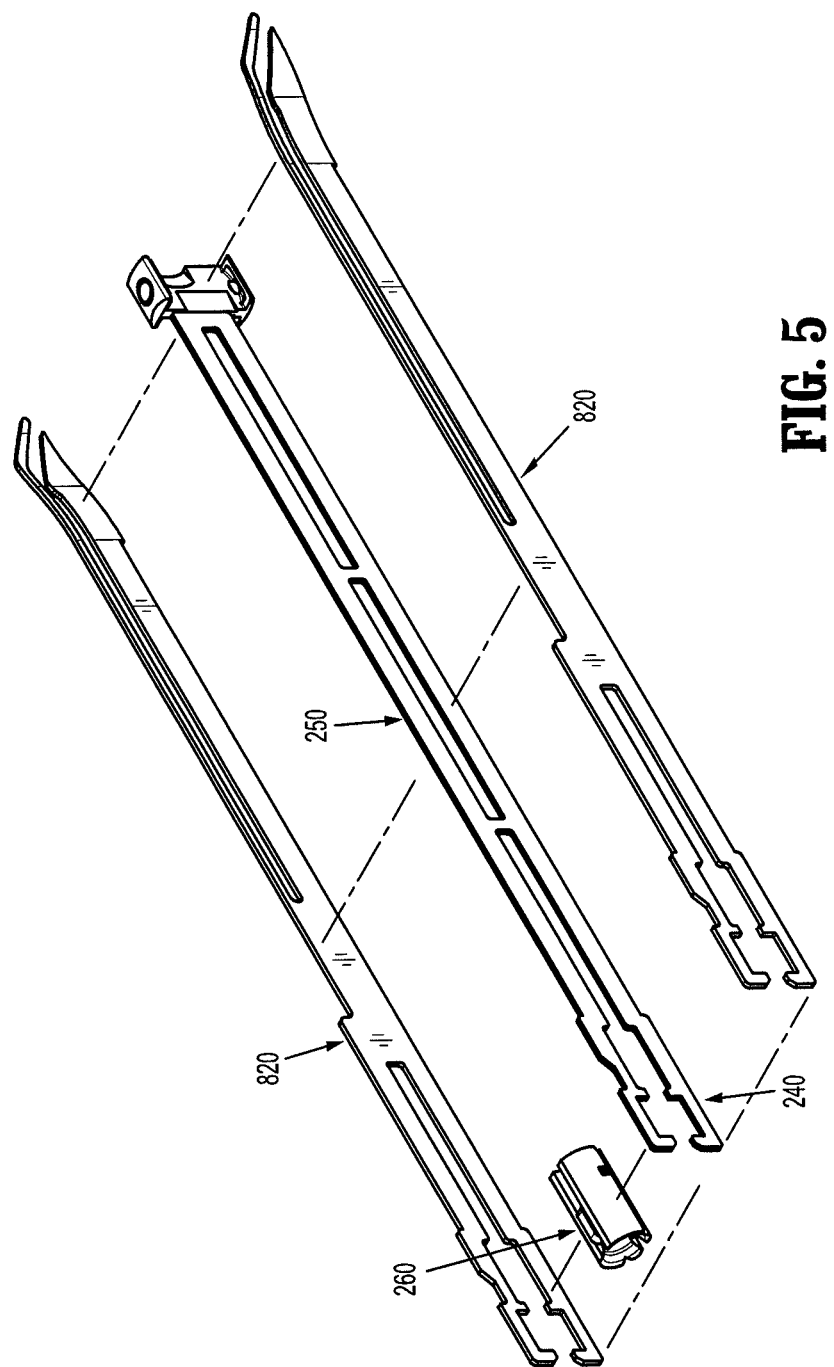

SURGICAL INSTRUMENT AND CARTRIDGE FOR USE THEREWITH

CROSS-REFERENCE TO RELATED APPLICATIONS

This application is a continuation of U.S. patent application Ser. No. 13/173,295 filed Jun. 30, 2011, now U.S. Pat. No. 8,763,876, and the disclosures of each of the above-identified applications are hereby incorporated by reference in their entirety.

BACKGROUND

1. Technical Field

The present disclosure relates generally to instruments for surgically joining tissue and, more specifically, to a surgical instrument that can be fired more than once without being required to reload fasteners.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical fasteners, an approximation mechanism for approximating the cartridge and anvil assemblies, and a firing mechanism for ejecting the surgical fasteners from the cartridge assembly.

Using a surgical instrument, it is common for a surgeon to approximate the anvil and cartridge members. Next, the surgeon can fire the instrument to emplace fasteners in tissue. Additionally, the surgeon may use the same instrument or a separate instrument to cut the tissue adjacent or between the row(s) of fasteners.

Additionally, a single use loading ("SULU") or a disposable loading unit ("DLU") may be attached to an elongated or endoscopic portion of a surgical stapling instrument. Such loading units allow surgical stapling instruments to have greater versatility, for example. The loading units may be configured for a single use, and/or may be configured to be used more than once.

Further, surgical instruments and/or loading units may include a cartridge that is removable and replaceable. For example, after all of the fasteners in a first cartridge have been ejected, a user may remove the first cartridge and replace it with a second cartridge including fasteners.

SUMMARY

The present disclosure relates to a cartridge assembly for use with a surgical instrument. The cartridge assembly comprises a cartridge housing and a cartridge. The cartridge housing has a plurality of biasing members thereon. The cartridge is configured for reception at least partially within the cartridge housing. The cartridge includes a plurality of fasteners at least partially therein. The cartridge has a plurality of pockets. Each fastener is ejectable from a corresponding pocket. The cartridge has a plurality of chambers therein, and each chamber is adjacent a pocket and is configured to store at least one fastener at least partially therein. At least one fastener is movable from the chamber to the pocket. The cartridge includes a plurality of pushers, where each pusher is configured to engage at least one corresponding fastener. At least one pusher includes at least one cam surface thereon. Each biasing member urges at least one corresponding fastener toward the corresponding pocket.

The present disclosure also relates to a loading unit configured for engagement with a surgical instrument. The loading unit comprising a proximal body portion defining a longitudinal axis, a tool assembly disposed in mechanical cooperation with the proximal body portion, and a cartridge assembly disposed in mechanical cooperation with the tool assembly. The cartridge assembly comprises a cartridge housing, a cartridge, and a driver. The cartridge housing has a plurality of biasing members thereon. The cartridge is configured for reception at least partially within the cartridge housing and includes a plurality of fasteners at least partially therein. The cartridge has a plurality of pockets, with each fastener being ejectable from a corresponding pocket. The cartridge has a plurality of chambers therein, and each chamber is adjacent a pocket and is configured to store at least one fastener at least partially therein. At least one fastener is movable from the chamber to the pocket. The cartridge also includes a plurality of pushers, and each pusher is configured to engage a corresponding fastener. Each biasing member urges at least one corresponding fastener toward the corresponding pocket. The driver is disposed in mechanical cooperation with the cartridge assembly, and is movable substantially parallel to the longitudinal axis into engagement with the pushers.

The present disclosure also relates to a surgical instrument comprising a handle assembly, a firing rod, an endoscopic portion, and a cartridge assembly. The handle assembly includes a movable handle. The firing rod is disposed in mechanical cooperation with the movable handle. The endoscopic portion extends distally from the handle assembly. The cartridge assembly is disposed adjacent a distal end of the endoscopic portion and comprises a cartridge housing, a cartridge, and a plurality of pushers. The cartridge housing has a plurality of biasing members. The cartridge is configured for reception at least partially within the cartridge housing. The cartridge includes a plurality of fasteners at least partially therein. The cartridge has a plurality of pockets. Each fastener is ejectable from a corresponding pocket. The cartridge has a plurality of chambers therein, and each chamber is adjacent a pocket and is configured to store at least one fastener at least partially therein. At least one fastener is movable from the chamber to the corresponding pocket. Each of the plurality of pushers is configured to engage a corresponding fastener. Each biasing member urges at least one corresponding fastener toward the corresponding pocket. Distal advancement of the firing rod causes sequential ejection of at least some of the fasteners.

The present disclosure also relates to a surgical stapling instrument comprising a cartridge assembly and an anvil assembly. The cartridge assembly has a cartridge body, a plurality of pushers supporting a plurality of fasteners in the cartridge body, and a driver longitudinally movable through the cartridge body in distal and proximal directions. The pushers have first cam surfaces and second cam surfaces. The anvil assembly has fastener forming surfaces. The driver has an upper portion and a lower portion. The upper portion of the driver contacts the second cam surfaces sequentially when the driver is moved in the proximal direction. The lower portion of driver contacts the first cam surfaces when the driver is moved in the distal direction.

BRIEF DESCRIPTION OF FIGURES

Various embodiments of the presently disclosed surgical instruments and loading units are disclosed herein with reference to the drawings, wherein:

FIG. 3 is a perspective view of a distal portion of the handle portion of FIG. 2;

FIG. 4 is a perspective view of a loading unit of the surgical instruments of FIGS. 1A and 1B;

FIG. 5 is a perspective exploded view of a clamping member and drivers of the surgical instruments of FIGS. 1A and 1B;

DETAILED DESCRIPTION

Figure 1A:
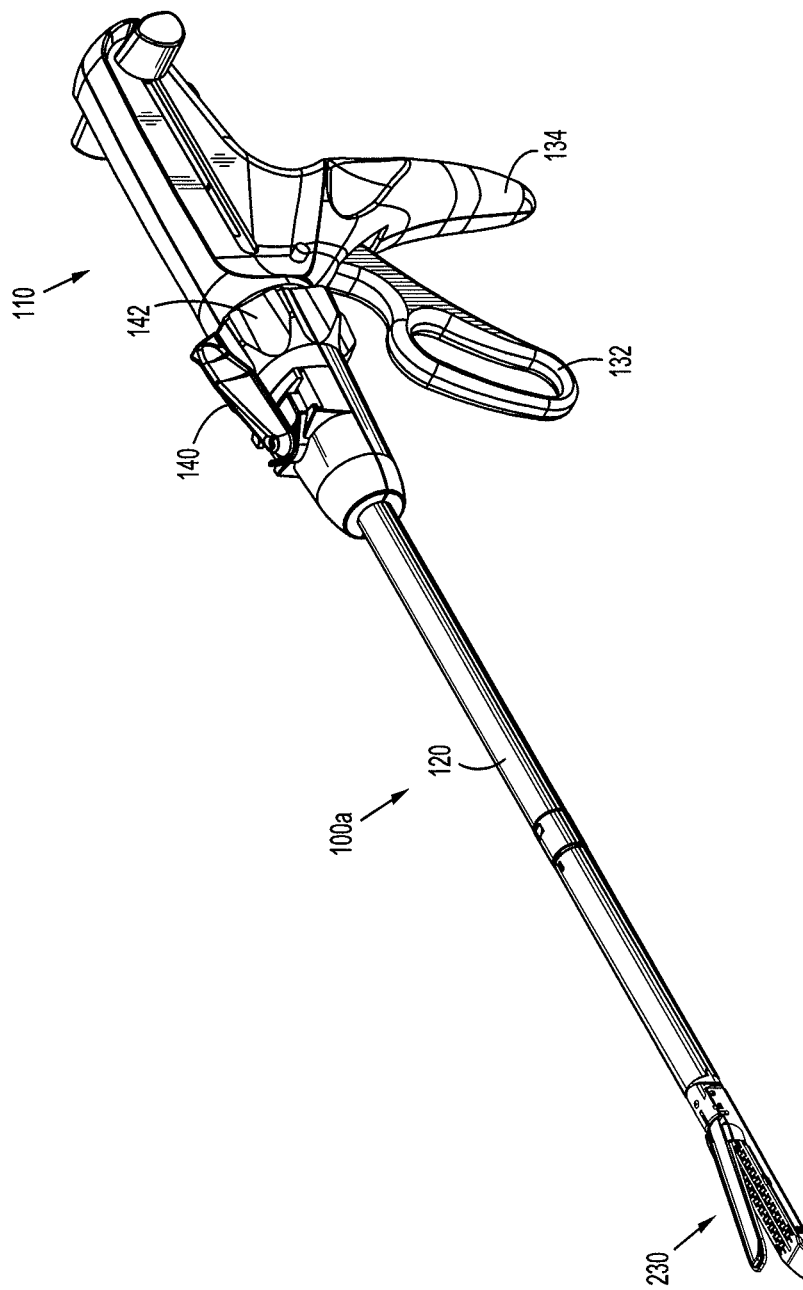
FIG. 1A is a perspective view of a surgical instrument in accordance with the present disclosure.

Embodiments of the presently disclosed surgical instrument, loading unit for use therewith, and cartridge assembly for use therewith, are described in detail with reference to the drawings, wherein like reference numerals designate corresponding elements in each of the several views. As is common in the art, the term "proximal" refers to that part or component closer to the user or operator, e.g., surgeon or physician, while the term "distal" refers to that part or component farther away from the user.

Figure 1B:
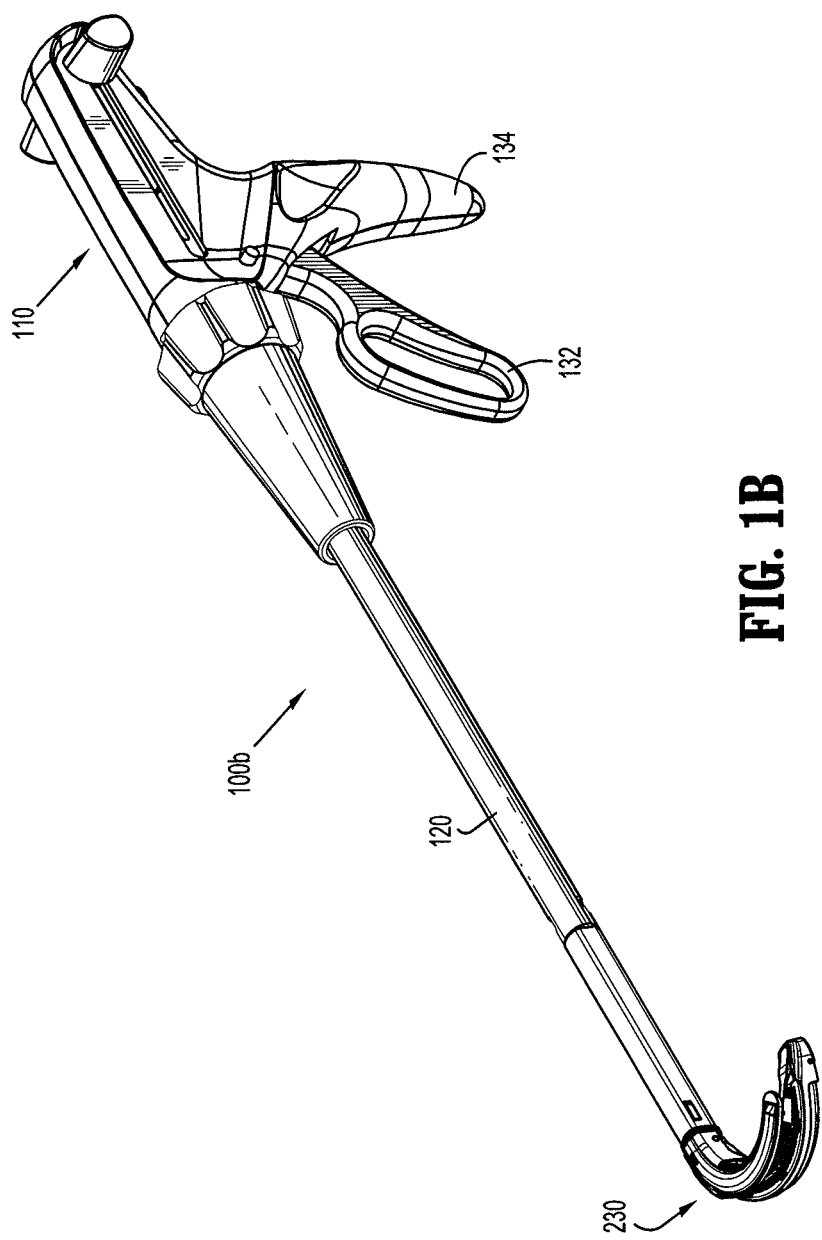
FIG. 1B is a perspective view of another surgical instrument in accordance with the present disclosure.

A surgical instrument having linear jaw members of the present disclosure is indicated as reference numeral 100a in FIG. 1A. A surgical instrument having curved jaw members of the present disclosure is indicated as reference numeral 100b in FIG. 1B. Collectively, surgical instruments 100a and 100b are referred to herein as reference numeral 100. Similarly, several features that are common to both surgical stapling instruments 100a and 100b are collectively referred to as the same reference number (e.g., handle portion 110, endoscopic portion 120, and jaw members 230).

Figure 2:
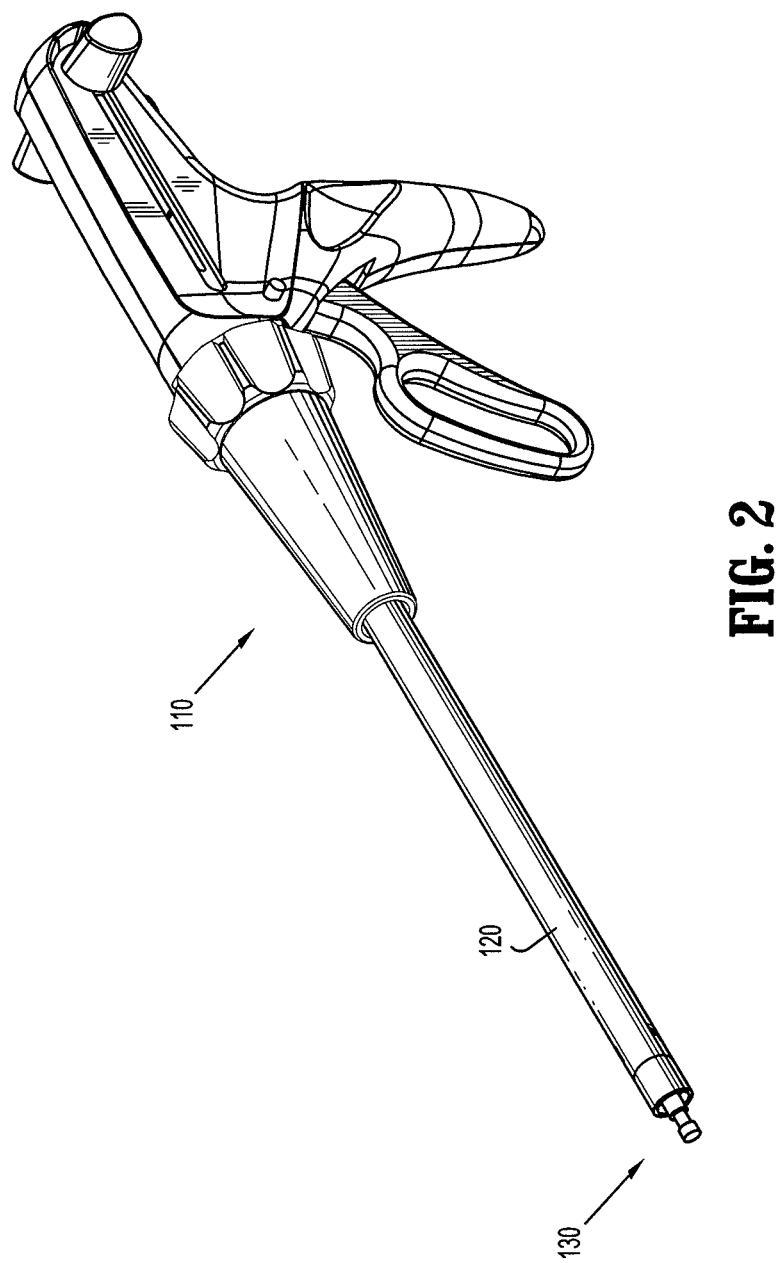
FIG. 2 is a perspective view of a handle portion of the stapling instruments of FIGS. 1A and 1B.
Figure 6:
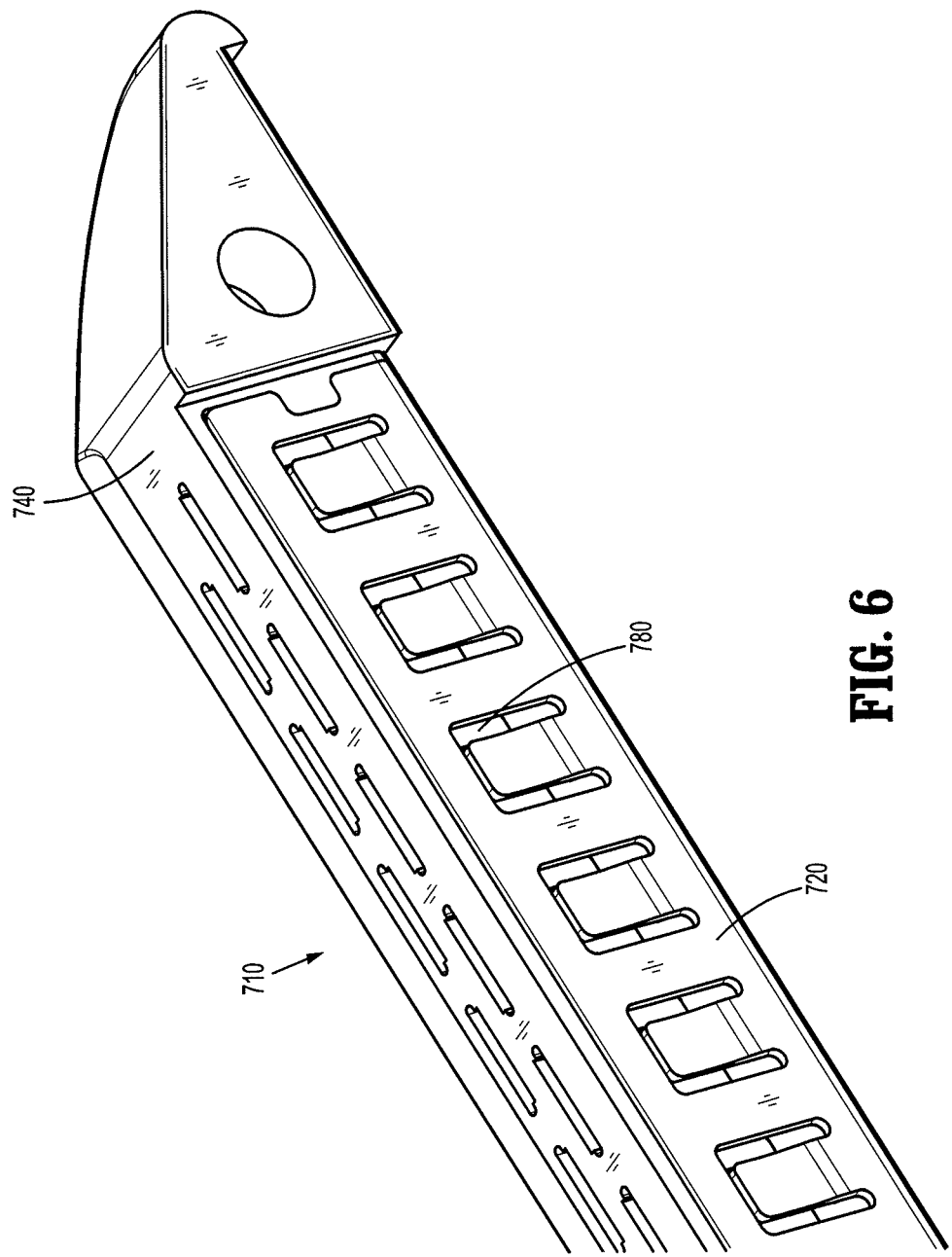
FIG. 6 is a perspective view of a portion of a cartridge assembly of the surgical instrument of the present disclosure.

Handle portion 110 of surgical instrument 100 is shown in FIG. 2, and an enlarged view of the distal end of handle portion 110, including a distal end of firing rod 130, is shown in FIG. 3. A single use loading unit ("SULU") or a disposable loading unit ("DLU") (collectively referred to as "loading unit 200"), which is mechanically engageable with handle portion 100 is shown in FIG. 4. Loading unit 200 is attachable to endoscopic portion 120 of surgical stapling instrument 100, e.g., to allow surgical instrument 100 to have greater versatility. Loading unit 200 may be configured for a single use, and/or may be configured to be used more than once. Alternatively, a surgical instrument may have a cartridge which is removable and replaceable in the reusable jaws of the instrument.

Examples of loading units for use with a surgical stapling instrument are disclosed in commonly-owned U.S. Pat. No. 5,752,644 to Bolanos et al., the entire contents of which are hereby incorporated by reference herein. Further details of an endoscopic surgical stapling instrument are described in detail in commonly-owned U.S. Pat. No. 6,953,139 to Milliman et al., the entire contents of which are hereby incorporated by reference herein.

In a surgical instrument 100 in accordance with the present disclosure, a firing rod 130 is moved distally through actuation of a movable handle 132 to deploy the fasteners. For example, referring back to FIGS. 1A and 1B, at least a partial actuation of movable handle 132 with respect a stationary handle 134 translates firing rod 130 longitudinally, such that a dynamic clamping member 240, its associated bar 250, and a proximal block 260 (e.g., FIG. 5) translates longitudinally, to approximate at least one jaw member with respect to the other. It is also envisioned that other types of handles can be used such as, for example, motor-driven, hydraulic, ratcheting, etc.

Figure 14:
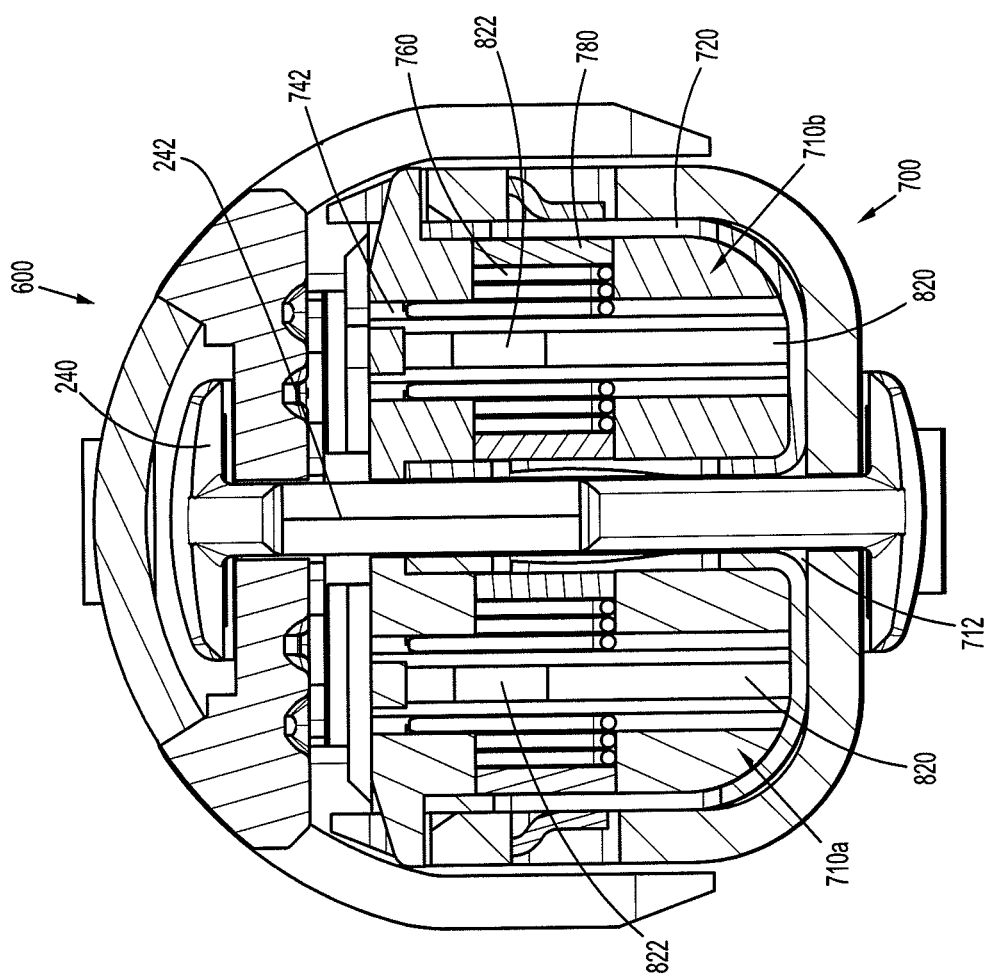
FIG. 14 is a transverse cross-sectional view of a tool assembly, including an anvil and a cartridge channel, and including two cartridge assemblies, two drivers, and the clamping member.

In the embodiment illustrated in FIG. 14, dynamic clamping member 240 includes an I-shaped cross-section, the top portion of which is configured to engage the anvil assembly, and the bottom portion of which is configured to engage the cartridge assembly. More particularly, engagement between the top portion of the dynamic clamping member 240 and the anvil assembly causes the anvil assembly to pivot towards the cartridge assembly, e.g., to clamp tissue therebetween. Continued distal translation of the dynamic clamping member 240 helps maintain the relative positions of the cartridge assembly and the anvil assembly with respect to each other.

Additionally, upon distal advancement, dynamic clamping member 240 advances drivers 820 through cartridge assembly 222. As the drivers 820 move distally, each driver 820 sequentially engages a plurality of pushers, and causes the pushers to move vertically within the cartridge assembly and eject fasteners 760 towards the anvil. The dynamic clamping member 240 may include a cutting edge 242 on a distal face of dynamic clamping member 240 to sever the stapled tissue. Subsequent to the ejection of fasteners 760, the stapled tissue is cut by the cutting edge 242 of the dynamic clamping member 240.

With reference to FIG. 4, loading unit 200 of the present disclosure is shown. Loading unit 200 includes a proximal body portion 210 defining a longitudinal axis "A-A," and a tool assembly 220 including a pair of jaw members 230. Proximal body portion 210 is configured to removably attach to endoscopic portion 120 of surgical instrument 100. More particularly, an insertion tip 202 of loading unit 200 is linearly inserted into the distal end of endoscopic portion 120 (FIGS. 2 and 3) of surgical stapling instrument 100. Nubs 204 of insertion tip 202 (FIG. 4) move linearly through slots (not shown) formed in the distal end of endoscopic portion 120. Subsequently, loading unit 200 is rotated about the longitudinal axis "A-A" such that nubs 204 move transversely through slots (not shown) within endoscopic portion 120. Additionally, during engagement of loading unit 200 and endoscopic portion 120, firing rod 130 of handle portion 110 engages dynamic clamping member 240 of loading unit 200 (see FIG. 5).

With reference to FIGS. 6-14, jaw members 230 of loading unit 200 include an anvil assembly 600 and a cartridge channel 700. In the illustrated embodiments, cartridge channel 700 houses a first cartridge assembly 710a and a second cartridge assembly 710b (collectively referred to as cartridge assembly 710), and includes a track 712 therebetween. Each cartridge assembly 710 includes a cartridge housing 720, a cartridge or cartridge body 740, a plurality of fasteners 760, a plurality of plates 780, and a plurality of pushers 800.

Figure 7:
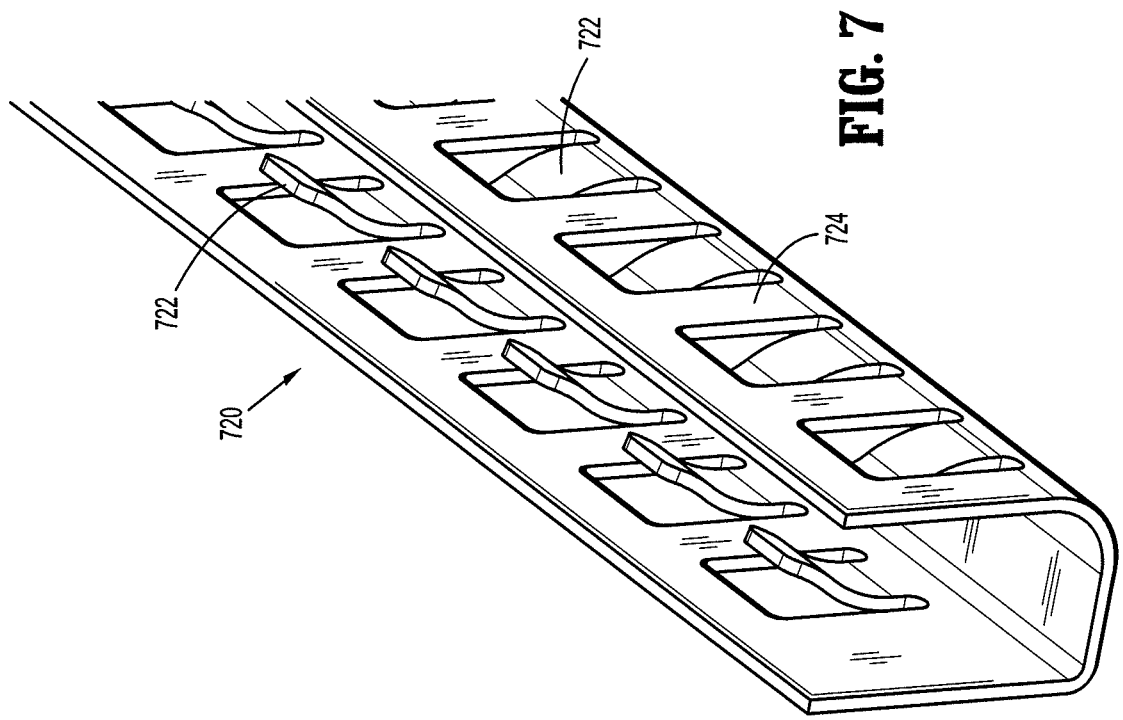
FIG. 7 is a perspective view of a portion of a cartridge housing of the cartridge assembly of FIG. 6.
Figure 8:
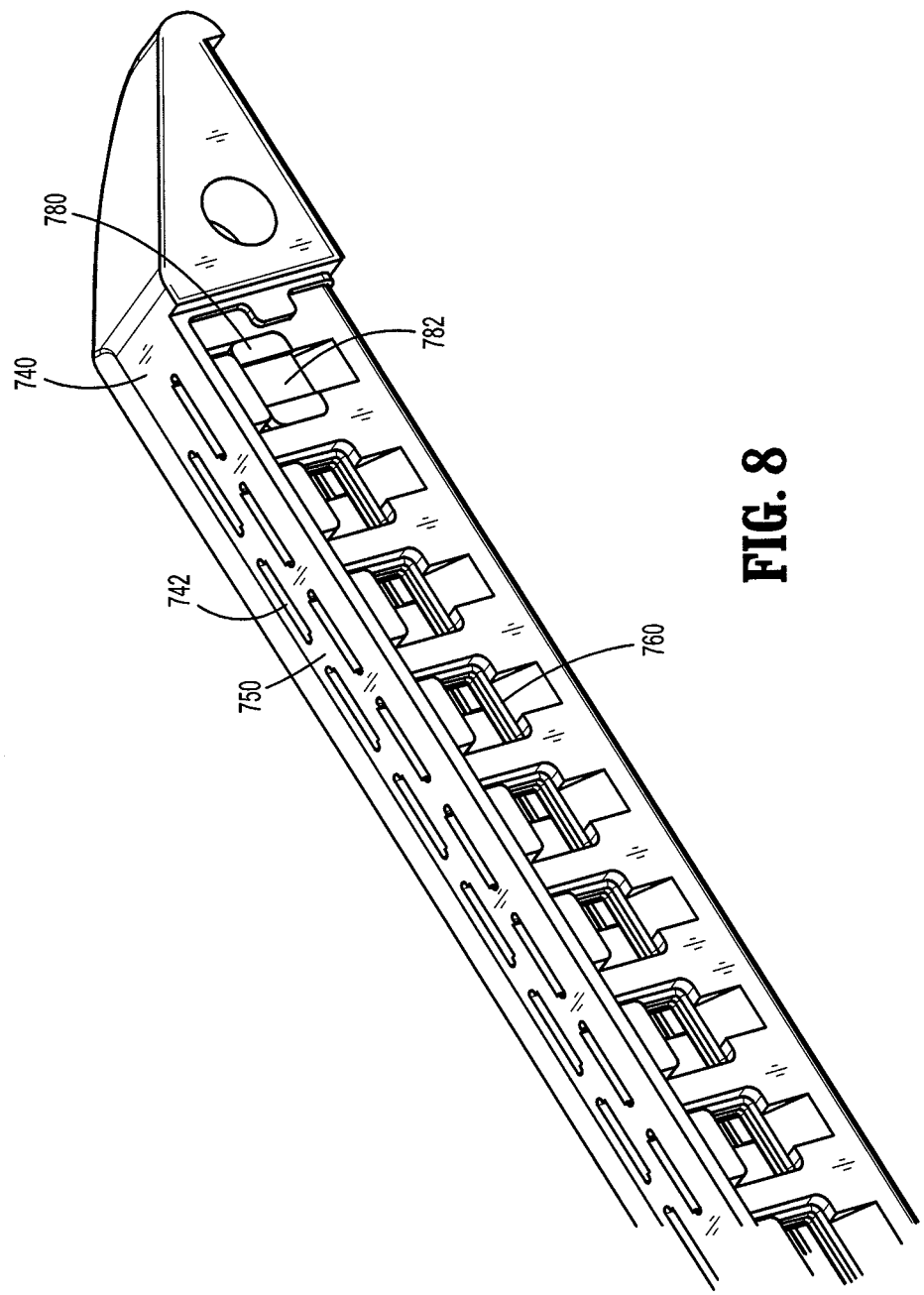
FIG. 8 is a perspective view of a portion of a cartridge, a plate and fasteners of the cartridge assembly of FIG. 6.
Figure 9:
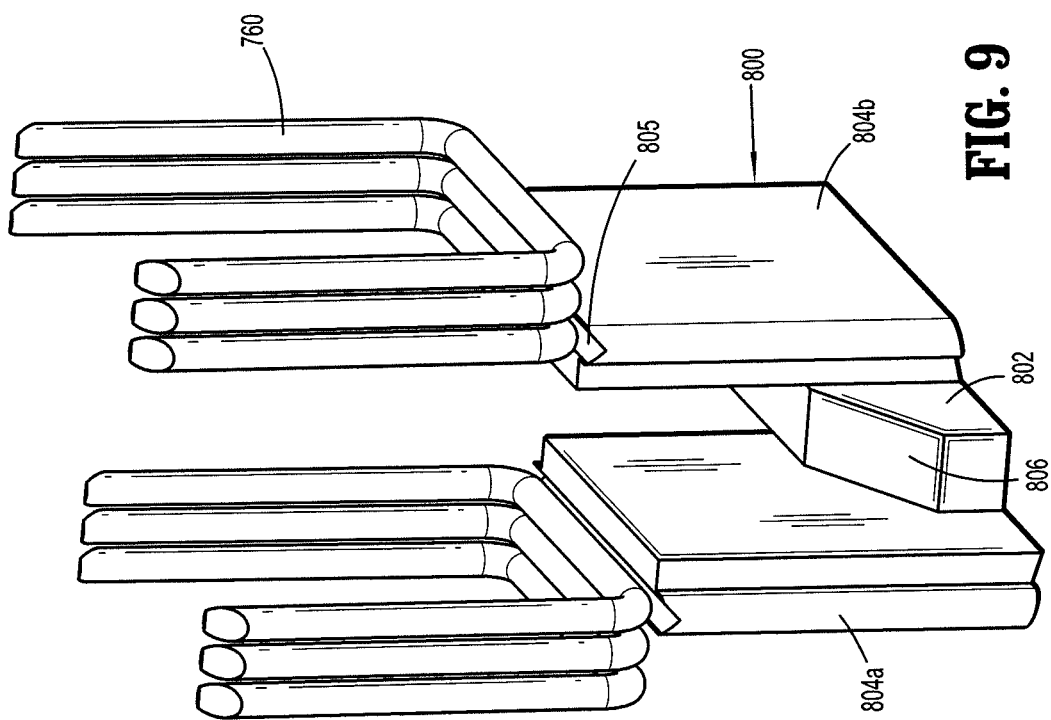
FIG. 9 is a perspective view of a pusher and fasteners of the cartridge assembly of FIG. 6.
Figure 10:
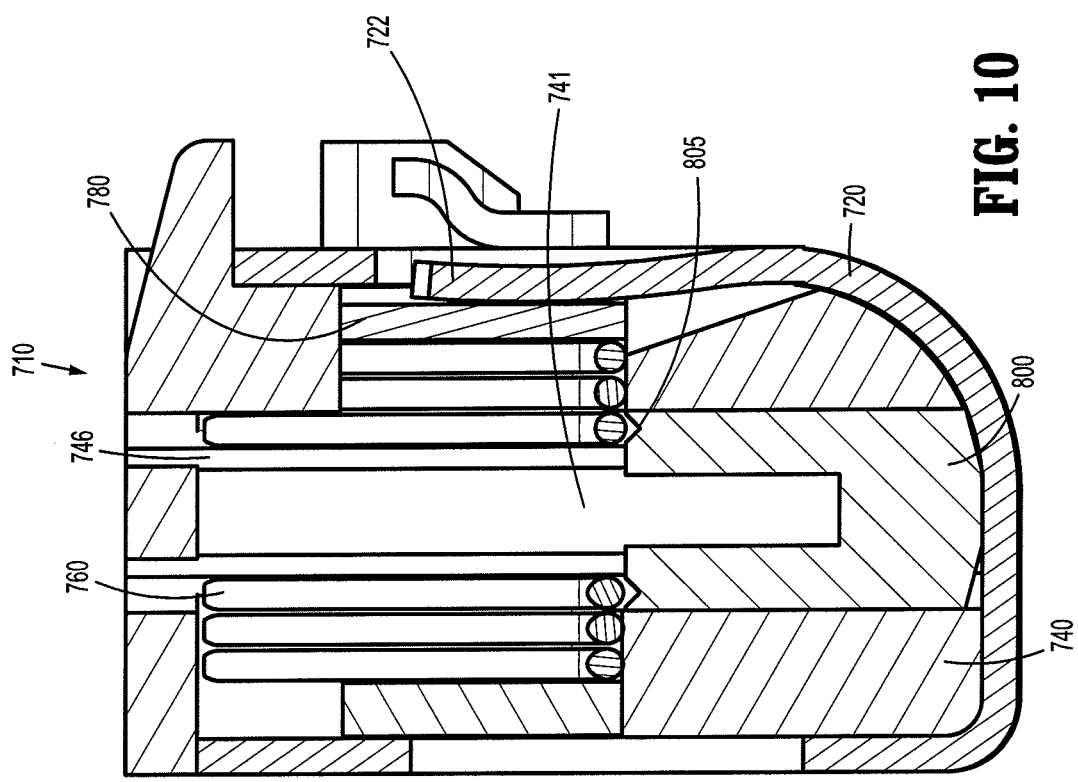
FIG. 10 is a transverse cross-sectional view of a portion of the cartridge assembly of FIG. 6 including a plurality of fasteners therein.

With particular reference to FIG. 7, each cartridge assembly 710a, 710b has a cartridge housing 720. One such cartridge housing 720 is shown. Cartridge housing 720 includes a plurality of biasing members 722 (e.g., leaf springs) thereon. Biasing members 722 are flexible fingers disposed on each side of the cartridge housing 710 and that are biased towards opposite side cartridge housing 720 (as shown in FIG. 7). Biasing members 722 are configured such that they are able to be against their bias into substantial alignment with an external wall 724 of cartridge housing 720 (see, for example, FIG. 10). As discussed below, each biasing member 722 is configured to bias a plate, and corresponding fasteners toward the opposite side of cartridge housing 720.

Figure 11:
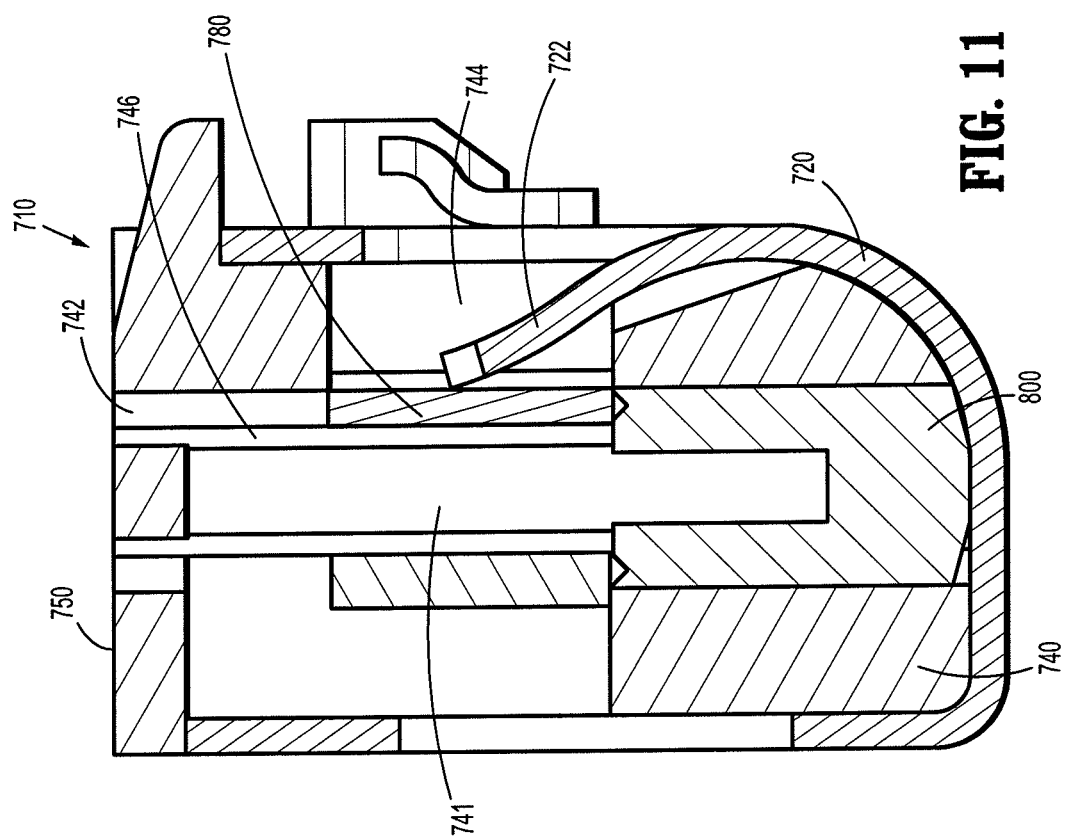
FIG. 11 is a transverse cross-sectional view of a portion of the cartridge assembly of FIG. 6 including no fasteners therein.

Referring now to FIGS. 8-11, cartridge or cartridge body 740, and components thereof, are illustrated. Cartridge or cartridge body 740 is configured for reception at least partially within cartridge housing 720 (FIG. 7) (e.g., a snap-fit connection) and includes a plurality of pockets 742, and a plurality of chambers 744 (FIG. 11). Each pocket 742 extends through a tissue-contacting surface 750 of cartridge body 740, and is configured to releasably store a fastener 760 that is ready to be fired. Each chamber 744 is adjacent a corresponding pocket 742 and is configured to store fasteners 760 therein (e.g., two fasteners 760). The configuration of pockets 742 and chambers 744 allows fasteners to move from chamber 744 to pocket 742 in response to the biasing force supplied by biasing members 722. An internal wall 746 of cartridge body 740 is adjacent pockets 742 and resists the biasing force, such that fasteners 760 do not get pushed beyond pocket 742.

With reference to FIGS. 6, 8, 10 and 11, plurality of plates 780 are shown. Plates 780 are disposed on the opposite side of chamber 744 than pockets 742. When fasteners 760 are present in cartridge body 740 (see FIG. 10), each plate 780 is between biasing member 722 and fastener 760. When no fasteners 760 are present in cartridge body 740 (e.g., after each fastener 760 has been fired; see FIG. 11), each plate 780 is between biasing member 722 and internal wall 746 (e.g., at least partially within pocket 742). Additionally, when no fasteners 760 are present in cartridge body 740, plates 780 block the path for advancement of pushers 800, thus preventing a user from firing/attempting to fire with an empty cartridge body 740. Plates 780 are sized to facilitate sliding within chamber 744 toward pocket 742. Additionally, and as shown in the embodiment illustrated in FIG. 8, plates 780 include a cut-out portion or indentation 782, which is sized to facilitate engagement with biasing member 722.

With particular reference to FIGS. 9-13, a plurality of pushers 800 and a plurality of fasteners 760 are shown. Each pusher 800 includes a central portion 802 and a pair of lateral portions 804a, 804b. Central portion 802 includes a first cam surface 806 and a second cam surface 808. As discussed below, each cam surface 806, 808 is configured to be engaged by a driver 820 to move pusher 800 toward and away from tissue-contacting surface 750 of cartridge body 740. Each lateral portions 804a, 804b is configured to engage a fastener 760, such that movement of pusher 800 toward tissue-contacting surface 750 of cartridge body 740 causes corresponding fasteners 760 to be ejected from cartridge body 740. In the illustrated embodiments, an upper surface 805 of lateral portions 804 includes a groove thereon (see FIGS. 9 and 10) to facilitate engagement with fastener 760.

Figure 12:
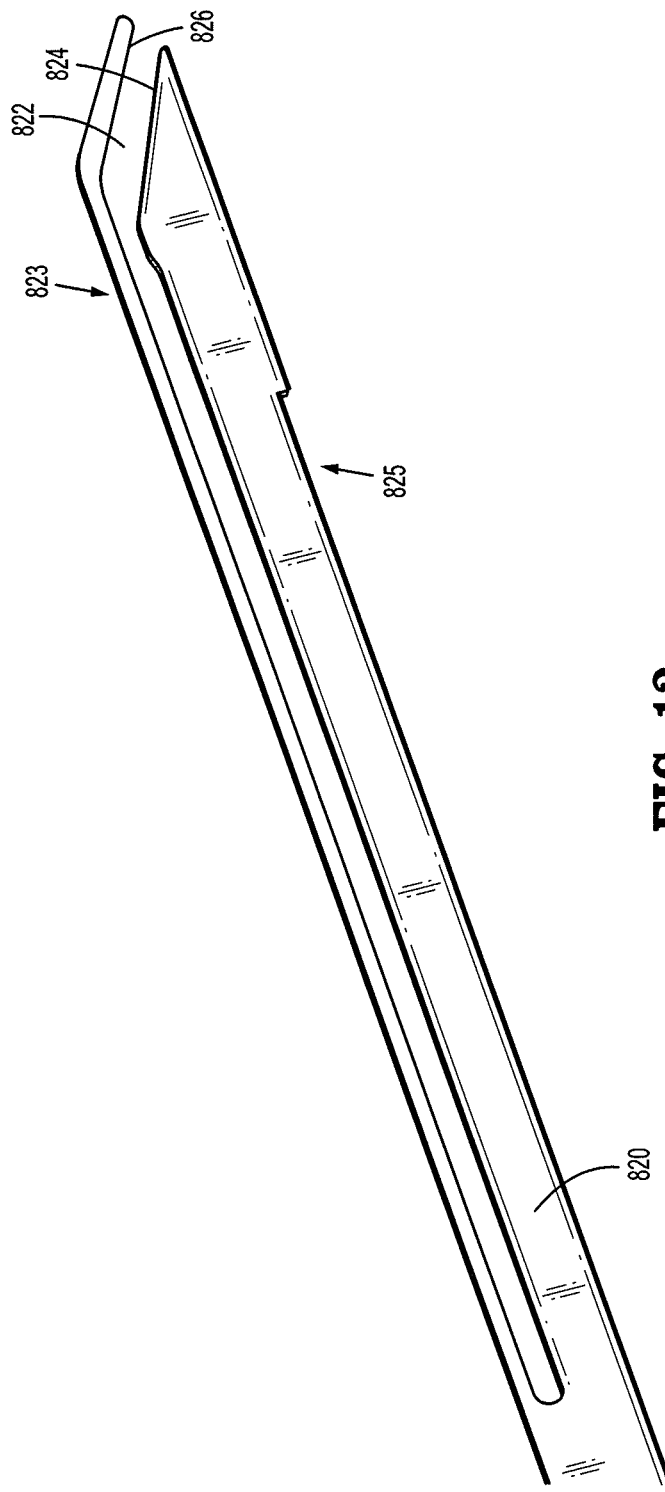
FIG. 12 is a perspective view of a portion of a driver of FIG. 5.
Figure 13:
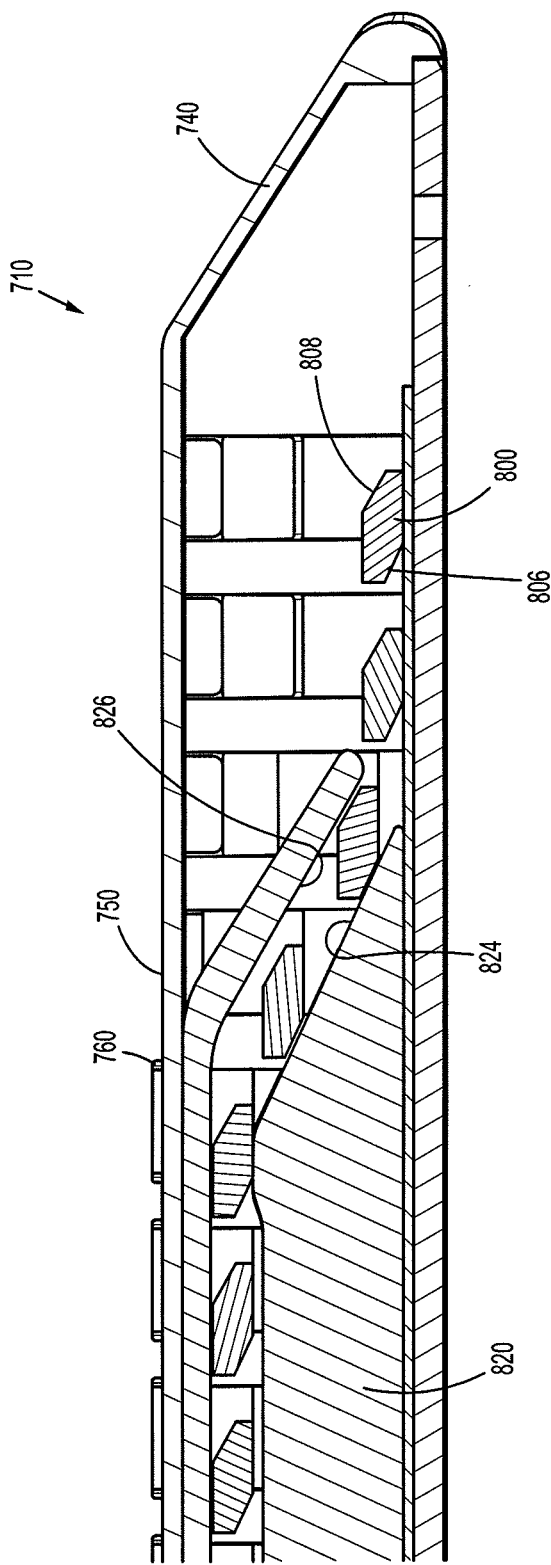
FIG. 13 is a longitudinal cross-sectional view of a portion of the cartridge assembly of FIG. 6 in combination with a portion of a driver.

Referring now to FIGS. 12-14 driver 820 is shown. Driver 820 is an elongated member that is configured to move longitudinally through a passage 741 (FIGS. 10 and 11) in cartridge body 740 in response to actuation of movable handle 132, for example. Driver 820 includes a slot 822 therein which separates an upper portion 823 from a lower portion 825. The slot 822 which extends proximally from a location adjacent a distal end thereof. Slot 822 includes a firing cam surface 824 and a retraction cam surface 826. Upon distal advancement of driver 820, firing cam surface 824 contacts first cam surface 806 of pusher 800, which causes pusher 800 to move toward tissue-contacting surface 750 (FIG. 13). Further movement of the driver 820 causes sequential ejection of the fasteners 760. Proximal movement of driver 820 causes retraction cam surface 826 to contact second cam surface 808 of pusher 800, which causes the pusher 800 to move away from tissue-contacting surface 750 (see FIG. 13). Further such movement of the driver 820 causes sequential retraction of the fasteners 760. Additionally, in the embodiment illustrated in FIG. 5, the driver 820 is rigidly attached to dynamic clamping member 240.

In use, actuation of movable handle 132 causes distal translation of dynamic clamping member 240, which causes distal translation of drivers 820. As drivers 820 advance distally, firing cam surfaces 824 of drivers 820 contact first cam surfaces 824 of pushers 800, which causes pushers 800 move toward tissue-contacting surface 750 of cartridge body 740. As shown in FIG. 13, pushers 800 sequentially move toward tissue-contacting surface 750 (i.e., the proximal-most pusher moves first, followed by the distally-adjacent pusher, etc.). Movement of pushers 800 toward tissue-contacting surface 750 causes corresponding fasteners 760 to be sequentially ejected from cartridge body 740. Here, after pushers 800 are elevated and within slots 822 of drivers 820, pushers 800 resist the force of corresponding biasing members 722, and thus prevent another fastener 760 from entering pockets 742 (i.e., the fasteners 760 remain in chambers 744). As the driver 820 is distally advancing and the fasteners 760 are being ejected from cartridge 710, a cutting element 242 (FIG. 14) of dynamic clamping member 240 cuts tissue between the jaw members 230.

After the driver 820 has been advanced a predetermined amount (e.g., corresponding to when all fasteners 760 have been ejected), a user may retract dynamic clamping member 240, and thus the driver 820. More than one driver 820 is contemplated herein. Retraction of driver or drivers 820 causes retracting cam surfaces 826 to contact second cam surfaces 808 of pushers 800, which causes pushers 800 to sequentially move away from tissue-contacting surface 750 of cartridge body 740. After pushers 800 have been moved away from tissue-contacting surface 750, pushers 800 no longer resist the force of corresponding biasing members 722, and thus biasing members 722 force another fastener 760 from chamber 744 into pocket 742.

Once drivers 820 have been retracted a predetermined amount (e.g., corresponding to when proximal-most fasteners 760 have been urged form chambers 744 into pockets 742), a user may repeat the process of advancing and retracting dynamic clamping member 240 and drivers 820 to eject another set of fasteners 760 without the need to replace cartridge channel 700 or cartridge assemblies 710. After all of the fasteners have been ejected from the cartridge assemblies, the plates 780 block the drivers from being advanced, and the clamping member 240 from being advanced, to prevent the firing of an empty cartridge. +

The illustrated embodiments illustrate three fasteners 760 in each pocket 742/chamber 744, but it is envisioned and within the scope of the present disclosure to include more or fewer fasteners 760 therein. It is also envisioned that at least one fastener 760 of cartridge assembly 710 is a different size from other fasteners 760. For example, it is envisioned that the inner row of fasteners (i.e., initially within pockets 742) includes fasteners having legs of a longest length, and that the outer row of fasteners includes fasteners having legs of a shortest length, or vice versa. Here, it is envisioned that the pushers 800 are sized accordingly.

The present disclosure also includes a method of firing a set of fasteners from a cartridge assembly, and then firing another set of fasteners from the same cartridge assembly without the need to remove and/or replace the cartridge assembly.

The present disclosure also includes embodiments having other types of handles than the illustrated embodiment. For example, the present disclosure also includes a powered (e.g., electrically-powered, battery-powered, etc.) handle.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A cartridge assembly for use with a surgical instrument, comprising:
   a cartridge housing having a plurality of flexible fingers; and
   a cartridge configured to be received at least partially within the cartridge housing, the cartridge including a tissue-contacting surface and a plurality of fasteners, the cartridge defining a plurality of pockets extending through the tissue-contacting surface, each one of the plurality of pockets configured to receive one of the plurality of fasteners, the cartridge having a plurality of chambers, each one of the plurality of chambers configured to receive at least one of the plurality of fasteners therein, each one of the plurality of chambers in communication with the respective one of the plurality of pockets,
   wherein each one of the plurality of flexible fingers urges the at least one of the plurality fasteners in the respective one of the plurality of chambers toward the respective one of the plurality of pockets.

2. The cartridge assembly according to claim 1, wherein the plurality of flexible fingers are disposed on opposing sides of the cartridge housing.

3. The cartridge assembly according to claim 2, wherein the plurality of flexible fingers on the opposing sides of the cartridge housing are biased toward each other.

4. The cartridge assembly according to claim 1, wherein the cartridge further includes a plurality of pushers, each one of the plurality of pushers configured to eject the respective one of the plurality of fasteners through the respective one of the plurality of pockets.

5. The cartridge assembly according to claim 4, further comprising a plurality of plates, each one of the plurality of plates operatively coupled to the respective one of the plurality of flexible fingers.

6. The cartridge assembly according to claim 5, wherein each one of the plurality of plates is configured to inhibit actuation of the respective one of the plurality of pushers in the absence of the respective one of the plurality of fasteners in the respective one of the plurality of pockets.

7. The cartridge assembly of claim 1, wherein the plurality of flexible fingers are leaf springs.

8. A loading unit configured for engagement with a surgical instrument comprising:
   a proximal body portion defining a longitudinal axis;
   a tool assembly disposed in mechanical cooperation with the proximal body portion; and
   a cartridge assembly disposed in mechanical cooperation with the tool assembly, the cartridge assembly including:
      a cartridge housing having a plurality of flexible fingers; and
      a cartridge configured to be received at least partially within the cartridge housing, the cartridge including a tissue-contacting surface and a plurality of fasteners, the cartridge defining a plurality of pockets extending through the tissue-contacting surface, each one of the plurality of pockets configured to receive one of the plurality of fasteners, the cartridge having a plurality of chambers, each one of the plurality of chambers configured to receive at least one of the plurality of fasteners therein, each one of the plurality of chambers in communication with the respective one of the plurality of pockets,
   wherein each one of the plurality of flexible fingers urges the at least one of the plurality fasteners in the respective one of the plurality of chambers toward the respective one of the plurality of pockets.

9. The loading unit according to claim 8, wherein the plurality of flexible fingers are disposed on opposing sides of the cartridge housing.

10. The loading unit according to claim 9, wherein the plurality of flexible fingers on the opposing sides of the cartridge housing are biased toward each other.

11. The loading unit according to claim 8, wherein the cartridge further includes a plurality of pushers, each one of the plurality of pushers configured to eject the respective one of the plurality of fasteners through the respective one of the plurality of pockets.

12. The loading unit according to claim 11, further comprising a plurality of plates, each one of the plurality of plates operatively coupled to the respective one of the plurality of flexible fingers.

13. The loading unit according to claim 12, wherein each one of the plurality of plates is configured to inhibit actuation of the respective one of the plurality of pushers in the absence of the one of the plurality of fasteners in the respective one of the plurality of pockets.

14. The loading unit according to claim 11, further including a driver disposed in mechanical cooperation with the cartridge assembly, the driver configured to engage the plurality of pushers.

15. The loading unit according to claim 14, wherein the driver is configured to sequentially engage the plurality of pushers.

16. The loading unit according to claim 8, wherein the plurality of flexible fingers are leaf springs.

17. The loading unit according to claim 8, wherein each one of the plurality of chambers is configured to receive three fasteners therein.

* * * * *